United States Patent
Budgett

(10) Patent No.: US 9,125,242 B2
(45) Date of Patent: Sep. 1, 2015

(54) SELECTABLE RESONANT FREQUENCY TRANSCUTANEOUS ENERGY TRANSFER SYSTEM

(75) Inventor: David Budgett, Auckland (NZ)

(73) Assignee: Millar Instruments Limited, Auckland (NZ)

( * ) Notice: Subject to any disclaimer, the term of this patent is extended or adjusted under 35 U.S.C. 154(b) by 1212 days.

(21) Appl. No.: 12/863,184

(22) PCT Filed: Jan. 20, 2009

(86) PCT No.: PCT/NZ2009/000005
§ 371 (c)(1),
(2), (4) Date: Jan. 5, 2011

(87) PCT Pub. No.: WO2009/091267
PCT Pub. Date: Jul. 23, 2009

(65) Prior Publication Data
US 2011/0101790 A1    May 5, 2011

(30) Foreign Application Priority Data
Jan. 18, 2008 (NZ) ........................................ 565234

(51) Int. Cl.
| | |
|---|---|
| H01F 27/42 | (2006.01) |
| H05B 6/06 | (2006.01) |
| H02J 17/00 | (2006.01) |
| A61M 1/12 | (2006.01) |
| H02J 5/00 | (2006.01) |
| H05B 6/08 | (2006.01) |
| A61B 5/00 | (2006.01) |
| A61N 1/378 | (2006.01) |

(52) U.S. Cl.
CPC ................. *H05B 6/06* (2013.01); *A61M 1/127* (2013.01); *H02J 5/005* (2013.01); *H02J 17/00* (2013.01); *H05B 6/08* (2013.01); *A61B 5/0031* (2013.01); *A61B 2560/0219* (2013.01); *A61F 2250/0001* (2013.01); *A61M 2205/3507* (2013.01); *A61M 2205/8243* (2013.01); *A61N 1/3787* (2013.01)

(58) Field of Classification Search
CPC ........... H05B 6/06; H05B 6/08; A61M 1/127; A61M 2205/8243; A61M 2205/3507; H02J 5/005; A61B 5/0031; A61B 2560/0219; A61F 2250/0001; A61N 1/3787
USPC ......................................................... 307/104
See application file for complete search history.

(56) References Cited

U.S. PATENT DOCUMENTS

| 5,293,308 | A |  | 3/1994 | Boys | |
|---|---|---|---|---|---|
| 5,831,348 | A | * | 11/1998 | Nishizawa | .................... 307/104 |
| 7,212,414 | B2 | * | 5/2007 | Baarman | ......................... 363/16 |
| 2007/0129767 | A1 | * | 6/2007 | Wahlstrand | ..................... 607/33 |
| 2009/0067207 | A1 | * | 3/2009 | Nishino | ........................ 363/126 |

FOREIGN PATENT DOCUMENTS

| NZ | 526115 | | 10/2006 | |
|---|---|---|---|---|
| NZ | 535012 | | 11/2006 | |
| WO | WO 2004/042750 | * | 10/2003 | ............. H01F 38/14 |
| WO | WO 2004/042750 | | 5/2004 | |

* cited by examiner

*Primary Examiner* — Daniel Cavallari
(74) *Attorney, Agent, or Firm* — Antoinette M. Tease

(57) ABSTRACT

An inductive power transfer system includes a number of controllable reactive components (3, 6, 12, 13, 16) that allow the resonant frequency of a primary and/or secondary resonant circuit to be controllably varied to thereby control power available to a load (10).

25 Claims, 5 Drawing Sheets

SELECTABLE RESONANT FREQUENCY TRANSCUTANEOUS ENERGY TRANSFER SYSTEM

FIELD OF INVENTION

The invention relates to inductive power transfer, and has particular relevance to adjusting the frequency of resonance of an inductive power transfer system to regulate power delivery and/or maximise system efficiency or power transfer.

BACKGROUND

Transcutaneous energy transfer (TET) systems are capable of transferring power across the skin without direct wire connections. This alleviates problems associated with infection at wire exit sites. A TET system will have a primary circuit including an inductive primary coil, located outside the body. The primary circuit generates a magnetic field. A secondary circuit, located inside the body, will include a secondary coil which couples with the magnetic field and the energy available is converted into power for the implanted device.

Because the coupling between the primary and secondary coils is usually low, a resonant circuit is implemented to provide power (voltage or current) amplification. A resonant circuit will have a natural resonant frequency which is dependent on the values of the capacitive and inductive components. For maximum power transfer, the resonant frequency of the secondary circuit should closely match the resonant frequency of the primary circuit.

Traditionally, the amount of power delivered to the implanted device is controlled by adjusting the strength of the magnetic field generated by the primary. An alternative approach is to adjust the resonant frequency of either the primary or the secondary away from the natural resonant frequency of the other part of the system. A miss-match in resonant frequencies will reduce the power delivered to the implanted device.

A mechanism for adjusting the reactive component (either resonant capacitor or resonant inductor) has been presented previously (in published New Zealand patent specifications NZ535012 and NZ526115) for the purpose of controlling power delivered to an implanted device. The method was based on switching a reactive component in and out of the circuit at the same rate as the resonant frequency to create an equivalent reactive element whose value is proportional to the phase of switching. Under this scheme, regulating the power requires switching at each cycle of the resonant frequency which creates power losses. Furthermore, the magnitude of the change in frequency that can be achieved is restricted by the harmonics introduced by the switching processes. This typically means that the value of the added effective capacitance is only a small proportion of the value of the fixed resonant capacitor, for example 20%.

SUMMARY OF INVENTION

It is the object of the present invention to provide an inductive power transfer system or a TET system which extends the range of frequencies at which the system resonates and/or lowers the power losses associated with switching reactive components every cycle. Alternatively, it is an object of the invention to provide an improved inductive power transfer system or a TET system, or to at least provide a useful alternative.

The performance of a TET system may be measured by different objective functions. An example of an objective function is to minimise the power losses. A second example is to maximise the amount of power transferred. A third example is to maintain the maximum temperature below a threshold. A fourth example is to ensure a minimum amount of power is transferred. Combinations of objective functions may be used to control the system. The system may change the objective function at different times in response to command signals or changes in measured parameters.

In broad terms, in one aspect the invention provides a primary circuit for an inductive power transfer system, the primary circuit comprising a resonant circuit, a plurality of discrete reactive components, and switching means operable to switch one or more of the reactive components into or out of the resonant circuit to deliver the correct power to substantially match a load demand.

Preferably the circuit includes an additional variable reactive component and means to further vary the power delivered as necessary using continuous control through cycle by cycle switching of the additional controllable reactive component.

Preferably the fine tuning range is sufficient to provide continuous variation in power delivery to a level that a new combination of discrete reactive component is switched in. At this new power level, fine tuning can again be used to further refine the power delivery if required.

Preferably the time that additional discrete controlled reactive components are switched in is much longer than the cycle-by-cycle time of the variable reactive component. The net effect is less power losses caused by lower currents passing through switching elements and lower loses in driving the inputs to the switching devices leading to improved system efficiency.

In another aspect the invention the switching of the reactive components is located at the secondary side of the circuit. The switching of reactive components may occur only at the secondary side. This accommodates multiple secondary circuits interacting with a common primary circuit.

Thus in another aspect the invention provides a secondary circuit for an inductive power transfer system, the secondary circuit comprising a resonant circuit, a plurality of discrete reactive components, and switching means operable to switch one or more of the reactive components into or out of the resonant circuit to deliver the correct power to substantially match a load demand.

Preferably the circuit includes an additional variable reactive component and means to further vary the power delivered as necessary using cycle by cycle switching of the additional variable reactive component.

In another aspect the invention provides variable reactive components on both the primary circuit and the secondary circuit. The system can operate at different resonant frequencies to maximise performance based on the relevant objective functions.

In one embodiment the primary and/or secondary circuit comprises a TET system.

The timing of the switching may be controlled by a microprocessor, an analogue circuit, programmable logic device or a combination of these circuits. The power requirement that determines the switching requirements can be derived from voltage, current, power or load information relating to the load demands and prevailing coupling conditions. Information can be supplied from the load to the switching control circuit using direct measurements, a telemetry link, or by signalling over the coupling channel of the inductive components.

In one embodiment of the system, the history of the load demand is used to determine the control method. If the load demand is changing frequently, then variable control is implemented. Once the load has reach a steady condition (e.g. varies by less than 10% over a period of several minutes), then the most appropriate discrete controlled components are activated, and variable control is implemented to allow for the difference between the discrete power delivery and the instantaneous power demand.

In one embodiment of the system the value of the discrete controlled reactive components are similar. This arrangement will incorporate redundancy and soft-fail performance. If one of the discrete switching circuits fails, then the system can detect this failure condition and use an alternative reactive component (or combination of components) to achieve the equivalent power delivery to the load.

In one embodiment of the system the discrete components are added to a primary circuit configured for series tuning resonance. In one embodiment of the system the discrete components are added to a primary circuit configured for parallel tuning resonance. In one embodiment of the system the discrete components are added to a secondary circuit configured for series tuning resonance. In one embodiment of the system the discrete components are added to a secondary circuit configured for parallel tuning resonance. The switching of the discrete controlled reactive components may be achieved using a bi-directional switch which may be of a semiconductor or a mechanical type.

In one embodiment the power management system has two main modes of operation. A first mode "normal" uses a first discrete controlled capacitor to provide power at a level suitable for operating the implanted device only. A second mode "high power" uses a second discrete controlled capacitor to provide power at a level suitable for both powering an implanted device associated with the secondary circuit and/or recharging a battery.

In another embodiment, discrete controlled capacitors are switched at both the secondary and primary sides to change from the "normal" to "high power" modes. This enables the system to have two sets of reactive components offering two power levels where power transfer occurs with very high efficiency.

In one embodiment, the power transfer rate is regulated based on the output of a temperature sensor. If the temperature exceeds a threshold, then the power transfer rate is reduced. With the presence of a microprocessor, an algorithm can have inputs including temperature, current medical device load demands, and battery fuel gauge information. Based on these inputs, the microprocessor can generate commands to match the power transfer rate to meet 1) the minimum power required to operate the device, independent of temperature, 2) supply power to operate the device up to its present load demand subject to the temperature being acceptable, 3) supply device and battery charging circuit subject to the temperature being acceptable. Suitable feedback mechanisms would be used to provide patient and care-provider information on which modes of operation are being used at different times. This feedback may include instructions for improving conditions such as improving coupling between primary and secondary coils. When a patient or care-provider is making adjustments to the system, real-time feedback on existing coupling conditions and further instructions for improving performance can be provided either visually, audibly or with tactile feedback.

In one embodiment, the primary is equipped with two battery packs. These packs can either be connected in parallel for operating in "normal" mode, or switched to be connected in series to provide a higher primary voltage to operate in "high-power" mode.

In one embodiment, the primary is equipped with two battery packs. These packs can either be connected in parallel for operating in "normal" mode when coupling is good, or switched to be connected in series to provide a higher primary voltage to operate in "low-coupling" mode when the coupling is poor. Optional feedback to the patient or caregiver may be provided when coupling is low.

In one embodiment, the primary conductor which provides a magnetic field to allow power to be induced in the secondary circuit is provided in the form of a coil. The conductor or coil may consist of a number of discrete sections of coil, and sections can be switched in to vary the total inductance. In this embodiment, the reactive element that is adjusted is the inductor (not the capacitor). This is another method of adjusting the resonant frequency and regulating the power flow. A further enhancement allows the selection of sections to provide adjustment to the orientation of the primary coil with respect to the secondary coil without needing to physically move the primary coil mechanism.

The invention may be used to power electrical devices inside the human body. In this application, the coupling between the internal and external components is subject to variations, and the adjusting of the frequency may be used to maintain a constant power supply to the device under changing coupling conditions.

In another aspect the invention provides an inductive power transfer system including: a primary power supply having a primary resonant circuit and being capable of providing an electromagnetic field; an inductive power pick-up having a pick-up resonant circuit and being capable of receiving power from the electromagnetic field provided by the primary power supply to supply power to an electrical load; a plurality of controllable reactive components, the controllable reactive components being associated with one or both of the primary resonant circuit and the pick-up resonant circuit; control means to increase or decrease the power available to the load by controlling one or more of the controllable reactive components to thereby vary the resonant frequency of the primary resonant circuit or the pick-up resonant circuit.

In another aspect the invention provides a method of inductive power transfer, the method including the steps of controlling the power available to a load by controlling a plurality of controllable reactive components associated with resonant circuits of one or both of a primary resonant circuit and a pick-up resonant circuit to vary the resonant frequency of the primary resonant circuit or the pick-up resonant circuit.

In another aspect the invention provides a method of inductive power transfer, the method including the steps of: controlling the power available to a load by controlling a plurality of controllable reactive components associated with one or both of a primary resonant circuit and a pick-up resonant circuit.

In another aspect the invention provides an inductive power transfer system including a primary power supply having a primary resonant circuit and being capable of providing an electromagnetic field; an inductive power pick-up having a pick-up resonant circuit and being capable of receiving power from the electromagnetic field provided by the primary power supply to supply power to an electrical load; a plurality of controllable reactive components, the controllable reactive components being associated with one or both of the primary resonant circuit and the pick-up resonant circuit; control means to increase or decrease the power available to the load by controlling one or more of the controllable reactive components to thereby vary the resonant frequency of the primary resonant circuit and/or the pick-up resonant circuit; control means to increase or decrease the power available to the load by controlling one or more of the controllable reactive components.

In another aspect the invention provides a method of delivering power to a load supplied by an inductive power transfer system, the method comprising switching one or more of a plurality of discrete reactive components into or out of a resonant circuit of the system such that the power delivered to the load substantially matches a load demand.

The invention also broadly consists of any novel feature or combination of features disclosed herein.

BRIEF DESCRIPTION OF DRAWINGS

The invention will be further described by way of example only, and without intending to be limiting, with reference to the accompanying drawings, wherein.

DETAILED DESCRIPTION

Figure 1:
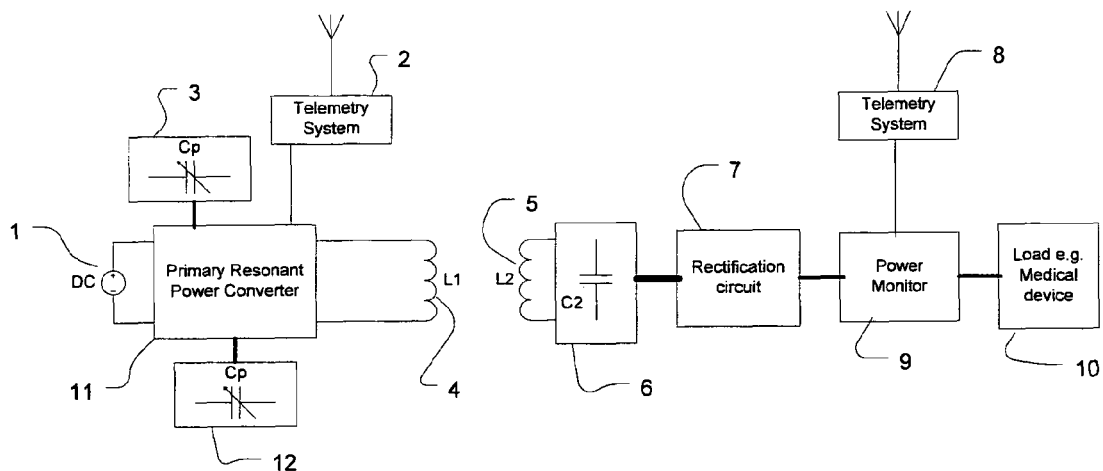
FIG. 1 is a block diagram showing the components of one embodiment of a transcutaneous energy transfer system incorporating the invention.

Referring to the drawings, like reference numerals are used to designate like components throughout the drawing figures. FIG. 1 shows one embodiment of an inductive power transfer (IPT) system in the form of a transcutaneous energy transfer (TED system for providing power from a primary circuit to a secondary, or pick-up, circuit which is closely associated with, and powers, an implanted device. As disclosed in NZ 535012 and NZ 526115, the primary circuit includes a resonant circuit consisting of a tuned conductor capable of providing a required electromagnetic field, such as coil 4. The secondary, or pick-up circuit includes secondary, or a pick-up, coil 5 which is tuned to provide a resonant pick-up circuit. The implanted device is represented by the load 10, and it may be a heart pump and/or battery charging circuit for example, or any other device that consumes electrical power. The implanted device may incorporate other parts of the TET system (5, 6, 7, 8, 9) into the same circuit and enclosure, and it may make use of telemetry services from telemetry system circuitry 8. Telemetry services can include sending data to a receiver outside the body, or receiving data from a transmitter giving command signals. The function of the implanted device might include monitoring of physiological signals, stimulation and/or actuation. This embodiment is arranged to adjust the resonant frequency of the primary circuit to ensure that the appropriate power is delivered to the load 10 under the prevailing load power demands and coupling conditions between the primary coil 4 and secondary coil 5.

The appropriate power is detected by Power Monitor circuit 9, this circuit detects the load demands of the device 10, the prevailing coupling conditions between coils 4 and 5, and can compensate for circuit parameters which may vary over time due to temperature, component tolerances, component aging, or component failure. A first controllable capacitor 3 is controllable to change the effective resonance capacitance to change the primary resonant frequency of the primary resonant circuit. If the primary resonant frequency matches the natural resonant frequency of the secondary circuit comprising the secondary coil 5 and secondary resonant capacitor 6 for the prevailing coupling conditions, then maximum power transfer will occur. If the primary resonant frequency is adjusted to be different from the natural resonant frequency of the secondary circuit, then less power is delivered to the load.

A second controllable capacitor 12 is also controllable to change the primary resonant frequency. Capacitor 12 operates with a slow response time compared to capacitor 3. The combination of the two "variable" capacitors 3 and 12 extends the options available for determining the frequency of operation. The power source 1 is essentially a constant DC voltage source. In practice, at times it will be a battery, and the applied voltage may reduce as the battery approaches exhaustion. The frequency of the primary converter may adjust to compensate for the reduced applied voltage. In one embodiment two battery packs (not shown) may be used which may be selectively connected in series or in parallel dependent on coupling or load conditions.

A telemetry system is shown in FIG. 1 including telemetry circuitry 2 (which may be part of the primary circuit), and telemetry circuitry 8 (which may be part of the secondary circuit) and provides an example of how the load power demands may be communicated to the primary circuit to allow for adjustment of the primary resonant frequency. Other data may also be transmitted by the telemetry system such as temperature, coupling condition and load device characteristics such as status of an internal battery. Other methods could be used to transfer the data including generating and monitoring perturbations on the coil voltage and current waveforms. Although the embodiment of FIG. 1 shows the controllable reactive component 3 located at the primary side, it could alternatively, or also, be located at the secondary side. This embodiment shows a controllable capacitive component 3. Another embodiment implements a variable inductive component. When implementing a variable inductive component, switching of different inductors, or coil sections, can be used to alter the effective orientation of the net inductive coil and enable control of the direction of the magnetic field vector, or simply alter the inductance in the resonant circuit. Alternatively, a core may be altered or moved relative to the coil to provide a controlled change in inductance. Similarly, a controlled capacitor may have a moveable plate portion to controllably vary the capacitance of the relevant resonant circuit. The rectification circuit 7 can consist of discrete diodes or synchronous rectifiers and may include reactive components. The primary resonant power converter 11 and/or secondary circuit 6 can be configured as series tuned or parallel tuned circuits.

Figure 2:
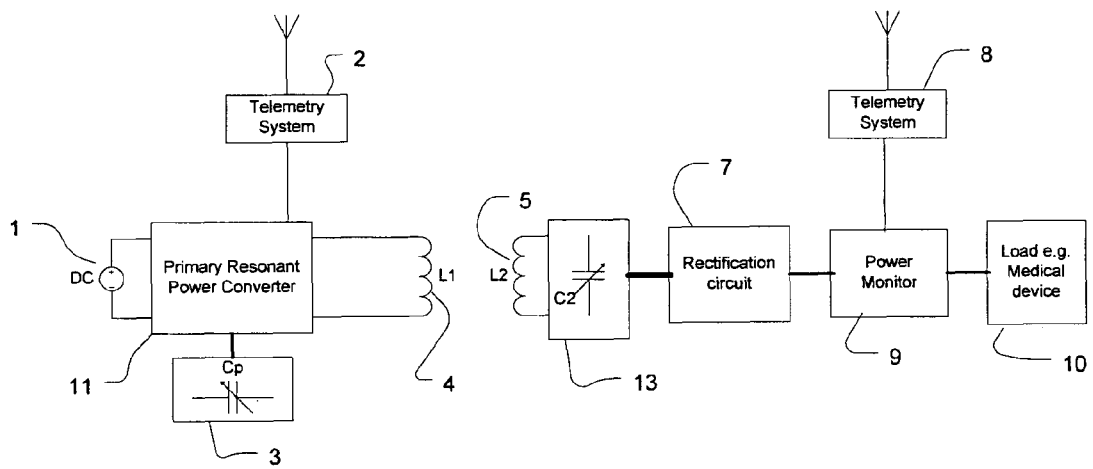
FIG. 2 is a block diagram showing the components of one embodiment of a transcutaneous energy transfer system where one controllable reactive component is located in the primary circuit, and a second controllable reactive component is located in the secondary circuit.

FIG. 2 shows a TET system where the resonant frequency of the secondary circuit is alternatively or additionally adjusted using the techniques described above. A controllable capacitive component 13 is used to change the resonant frequency of the secondary circuit. In this circuit the resonant frequency of the secondary and the resonant frequency of the primary can both be adjusted together, or independently. In this embodiment, the controllable reactive components 3 and 13 may be implemented using a similar circuit topology. Thus, controlled reactive components may be used in either, or both of the primary and secondary circuits.

Figure 3:
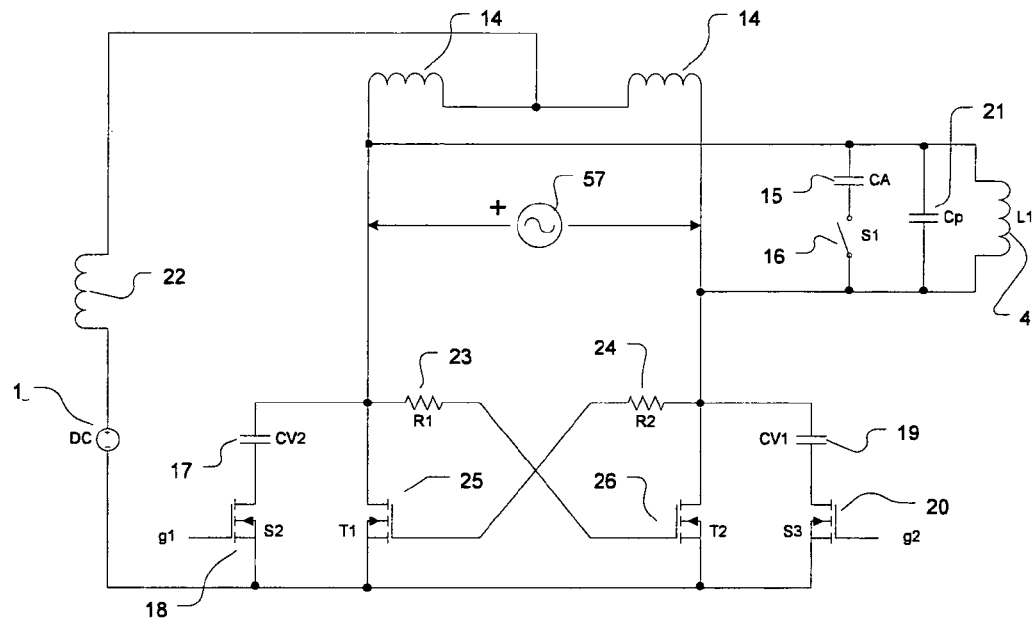
FIG. 3 shows a schematic diagram of a circuit capable of adjusting the operating frequency of the primary circuit by both discrete jumps and continuous adjustment.

FIG. 3 shows a schematic diagram of a practical circuit that adjusts the primary resonant frequency in response to a control signal. The primary controller of FIG. 3 includes a DC power source 1, a direct current inductor 22, a splitting transformer 14, a primary coil 4, a fixed resonant capacitor 21, an additional resonant capacitor 15, a switch 16 to connect capacitor 13 into or out of the circuit, a self-oscillating crossover circuit comprising components 23, 24, 25, 26, and two variable capacitor arms, the first consists of capacitor 19 and switch 20 and is active on negative sections of the resonant cycle, and the second arm consists of capacitor 17 and switch 18 and active on positive sections of the resonant cycle. The resonant cycle is indicated in FIG. 3 by the presence of oscilloscope 57 which measures the voltage across the primary coil 4. Oscilloscope 57 serves the purpose of illustrating the timing of the control signals to achieve frequency variation.

This circuit requires three signals to control switches 16, 18 and 20. On start up all switches are off and the primary circuit resonates at a frequency determined by coil inductance 4 and capacitor 21. A discrete step in resonant frequency occurs when switch 16 is turned on, the new resonant frequency is now determined by the coil inductance 4 and the parallel combination of capacitors 21 and 15. Continuous variation of frequency is achieved by switching 18 and 20 at the correct phase during each cycle.

When implementing variable frequency power regulation, switch 18 will be turned on for part of the waveform when 24 shows a positive cycle. During this positive half cycle, switch 26 is fully on, and for the duration switch 18 is on, capacitor 17 will be effectively connected in parallel with capacitor 21. Switch 18 is turn off again before the end of the positive half cycle. During the negative half cycle shown on the oscilloscope, switch 25 is fully on, and for a proportion of the negative half cycle, switch 20 will be turned on with the effect that capacitor 19 will be connected in parallel to capacitor 21. By adjusting the proportion of the time that switches 18 and 20 are on during their respective half cycles, the effective capacitance can be controlled and this will change the resonant frequency of the primary circuit. By switching 18 on and off at the same voltage measured by 57, zero current switching is achieved. The same argument applies to switch 20.

Figure 4:
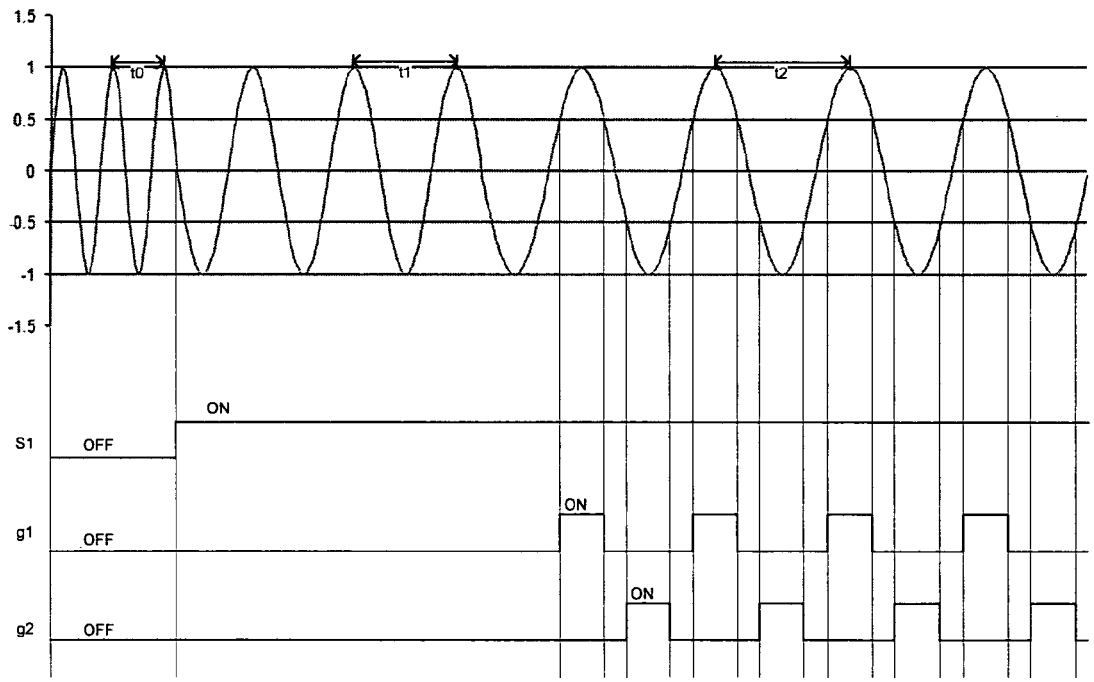
FIG. 4 shows the switching waveforms for a primary circuit providing three different power levels to a device under consistent coupling conditions.

FIG. 4 shows the timing of the switches used to create three different resonant frequencies. The period of the first frequency is shown in FIG. 4 as t0 and occurs with the switches 16 (controlled by signal s1), 18 (controlled by signal g1), and 20 (controlled by signal g2) all off. The period of the second frequency is shown as t1 and occurs when 16 is turned on. In this situation, t1 is maintained without any additional switch transitions.

An illustration of variable frequency adjustment is given by the frequency represented by the period t2. To generate this frequency, 18 (g1) is turned on for a proportion of each positive half cycle, and 20 (g2) is turned on for a proportion of each negative half cycle. By increasing the proportion of the on time during the positive half cycle, the effective capacitance will increase, and this will reduce the resonant frequency. In FIG. 4, the time that g1 is turned on is determined by the primary coil voltage reaching 50% of the peak magnitude of the primary coil resonant voltage. Similarly, the time that g1 is turned off is determined by when the primary coil resonant voltage falls below 50% of the peak. Setting the threshold between 0 and 100% determines the effective change in the reactive component value contributing to determining the resonant frequency.

Figure 5:
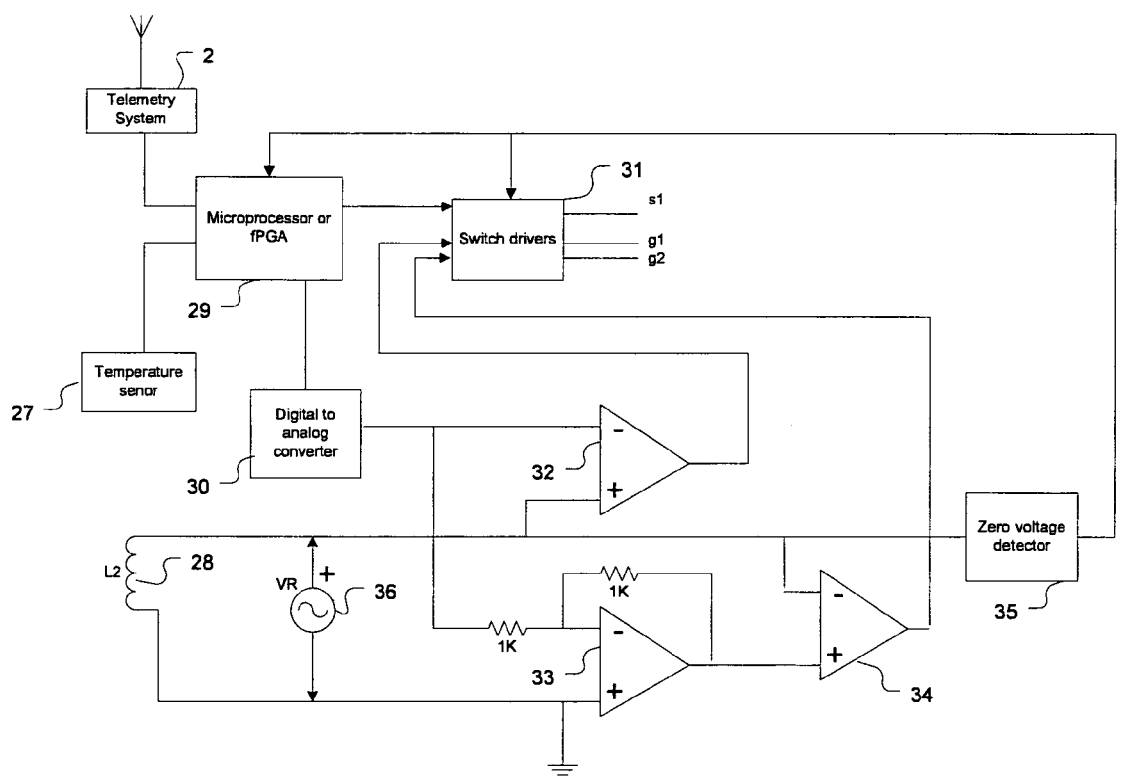
FIG. 5 shows a schematic of a circuit capable of generating the signals to control the switching of the reactive components based on a range of input signals.

FIG. 5 gives a simplified example of how the switch control signals are generated. The telemetry system 2 receives information about the operating conditions of the load. This information might include load power demand, power being received over the TET system and temperature at various locations. The current status of the resonant circuit is available from a coil 28 which is producing a voltage signal VR 36 which is synchronised to the voltage across the primary coil inductor. VR is able to be used by the Zero Voltage Detection (ZVD) circuit 35 to ensure that the timing of the switching is done to achieve soft switching and minimise power losses.

For example, s1 will be gated with the command to turn on from the processor unit 29 and the signal from the ZVD 35 such that the voltage across the primary coil is zero at the time switch 16 from FIG. 3 is activated. The processor unit 29 could be a microprocessor, discrete logic or a programmable gate array. When the load status is appropriate, the processor unit will enable variable frequency switching.

The processor unit generates a threshold analogue signal using the digital to analogue converter 30. When the voltage VR exceeds the threshold, opamp 32 generates the control signal for g1 to turn on. When the voltage VR drops below the threshold, g1 will turn off. Opamps 33 and 34 generate the equivalent control signal for g2 during the negative half cycle.

The switch driver 31 converts the digital control signals into signals for driving the switches. These switches may be a combination of solid-state semiconductors and mechanical switches. The switch driver implements isolated gate drives if required. Additional features are not shown in FIG. 5. This includes the ability to use hard switching to facilitate start-up functions.

A temperature sensor 27 is also shown in FIG. 5. This optional sensor can provide additional information to determine the power level that can be transferred without causing overheating. Other potential locations for temperature sensors include the secondary coil, batteries, medical devices and circuit boards. Remote temperature data is available at the controller in FIG. 5 through the Telemetry System 2. When coupling conditions and device load requirements permit, power transfer levels are regulated for the purpose of recharging batteries based on acceptable temperature levels.

The circuit shown in FIG. 3 shows a single discrete reactive controlled component 15 under control of switch 16. If a second discrete controlled reactive component, of the same value as 16, and with an independent switch, is added in parallel, then redundancy is introduced to the system. In this configuration the failure of a discrete component or control switch representing an open circuit can be corrected by using the remaining functional elements. The selection of components can be determined to provide multiple options for delivering critical power levels (for example to maintain device function). Furthermore, if appropriate discretely controlled reactive components are provided on each of the primary and secondary, then two fundamental frequencies of operation are possible, and these may correspond to two different power transfer levels.

Thus one embodiment of the invention provides an inductive power transfer system (and in particular a TET system)

for which frequency ranges are selected for different power ranges, and variable frequency adjustment is performed within each discrete power range. The controllable component 15 provides control between at least two discrete frequency ranges, and components 17 and 19 allow control over further frequency ranges which are preferably within the discrete frequency ranges. Therefore, the slower response component 15 which is intended to be connected over a large number of cycles of the resonant current or voltage, provides a coarse frequency adjustment. The fast response components 17 and 19 are switched into and out of the circuit on a cycle-cycle basis, and allow a fine frequency adjustment. It will be seen that coarse frequency adjustment may be provided on one of the primary or secondary and fine frequency on the other, if required.

Figure 6:
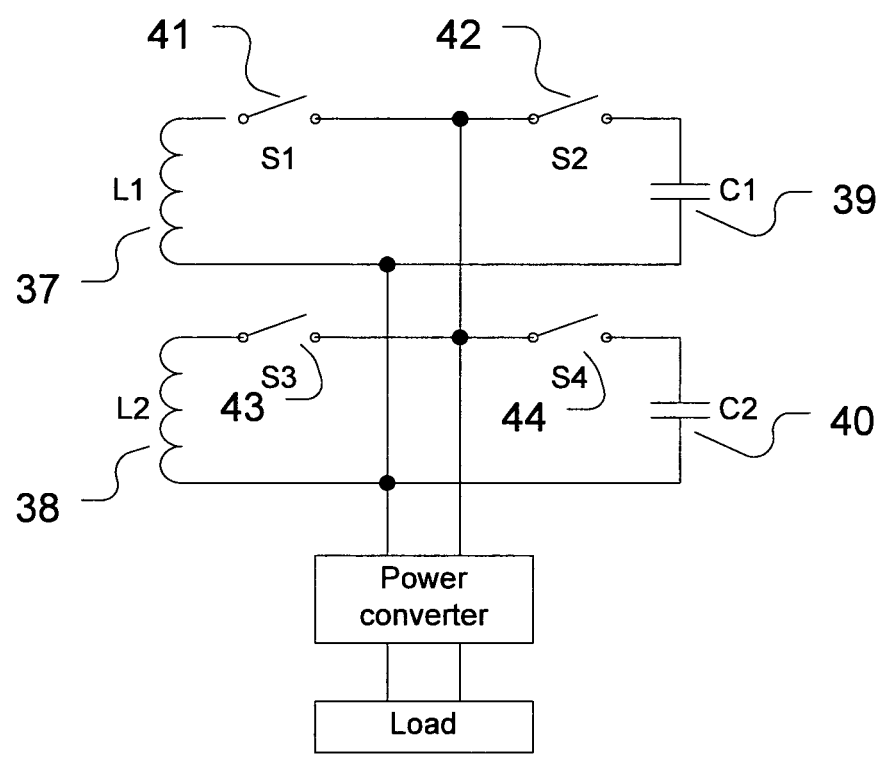
FIG. 6 shows a schematic of a secondary circuit with multiple reactive components providing a range of frequencies and component redundancy for a parallel tuned circuit.

The circuit in FIG. 6 illustrates how a variable capacitor can be implemented with switches and two capacitors C1 39 and C2 40. When S2 42 is open and S4 44 is closed, the equivalent capacitive component of the parallel resonant circuit presented to the power converter comprises of C2 only (assuming ideal components). If switch S2 42 is closed and S4 44 is closed, the equivalent capacitance increases to C1+C2. If switch S2 42 is open, and switch S4 44 is closed, the equivalent capacitance is C1. Similarly, the status of switches S1 and S3 determine the equivalent inductance of the parallel resonant circuit presented to the power converter. If S1 41 is closed and S3 43 open, the equivalence inductance is equal to L1. If S1 41 is closed and S3 43 is closed, the equivalent inductance is equal to L1*L2/(L1+L2). If S1 41 is open and S3 43 closed, the equivalent inductance is equal to L2. If L1 is not equal to L2, and C1 is not equal to C2, then there are nine different combinations of capacitor and inductor values that can comprise the resonant circuit presented to the power converter. Therefore, the switching matrix of switches S1-S4 allows selective connections to be made such that a plurality of different configurations of reactive elements are possible.

The selection of which set of values will be used will be determined by the state of switches S1, S2, S3 and S4. The selection may depend on a combination of factors including the amount of power transfer required, the prevailing coupling conditions and the temperature of the components. If C1 is equal to C2 and L1 is equal to L2, then the number of combinations of capacitor and inductor values is reduced to four, however, the matched capacitors and inductors can provide redundancy in the case of failure of any single element. A useful circuit could be constructed with L1, C1 and C2 with two switches S2 and S4. In this configuration, L1 represents the inductive resonant element, and switches S2 and S4 determine the capacitive element. If C1 and C2 are equal, the circuit has built in redundancy for failure of a capacitive element.

Figure 7:
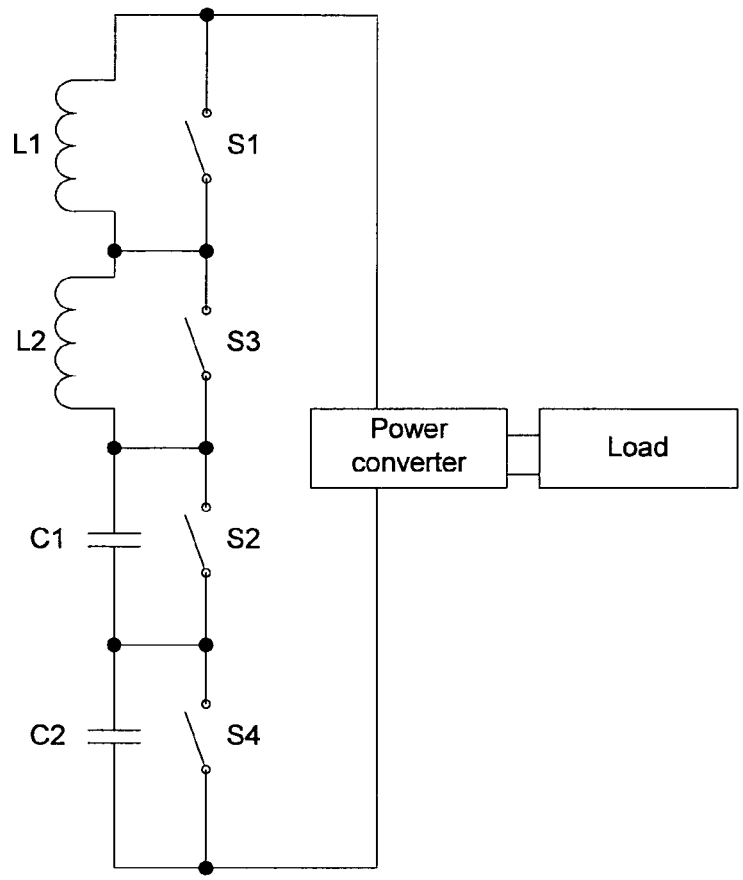
FIG. 7 shows a schematic of a secondary circuit with multiple reactive components providing a range of frequencies and component redundancy for a series tuned circuit.

FIG. 7 illustrates how the equivalent capability could be implemented as a series resonant circuit.

Figure 8:
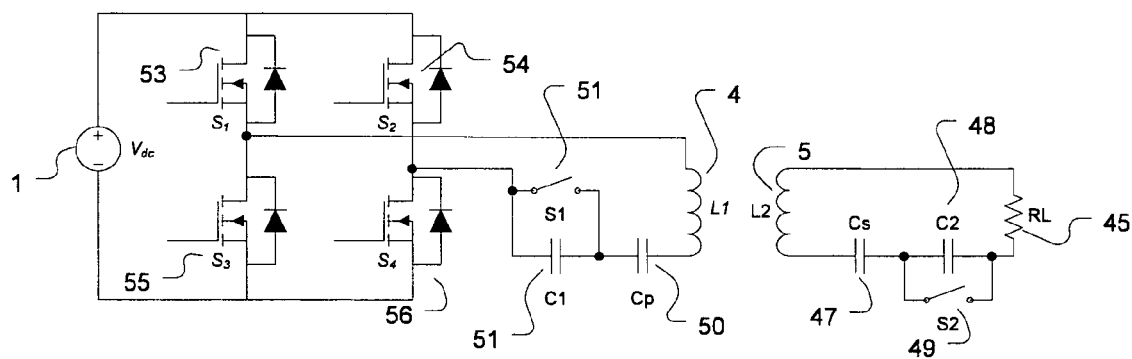
FIG. 8 shows a practical circuit that implements variable reactive components in both primary and secondary circuits to switch from high power to high efficiency modes of operation.

A practical circuit of a TET power delivery system is given in FIG. 8. The DC power source 1 is set to 15V, the load 45 is a 2 Ohm resistor. Both inductors L1 4 and L2 5 are 22 uH, and the coupling coefficient between the two coils is 0.2. The capacitor Cp 50 is 44 nF and the capacitor Cs 47 is 55 nF. The capacitor C1 is 314 nF and the capacitor C2 48 is 131 nF. A full bridge drive circuit consists of MOSFETS 53, 54, 55 and 56 and these devices are driven by signal generator outputs at a frequency that achieves zero voltage switching (170.3 kHz). When the circuit is operated in mode 1 with switches S1 51 and S2 49 off, the power delivered to the load is 13.3 W with an efficiency of 84% (i.e. a low or non-maximal power transfer level at a high or maximum efficiency). When the circuit operates in mode 2 with switches S1 51 and S2 49 on, the power delivered to the load is 45.8 W with an efficiency of 46% (i.e. a high or maximum power transfer level at a low or non-maximal efficiency). When operating in mode 2 the majority of losses are occurring from the primary circuit. At the primary circuit there are many options for managing heat dissipation. This circuit offers a high power transfer mode and a low power transfer mode. Although reactance changes occur in the resonant circuit(s), it is still possible for the system to have the same resonant frequency.

The foregoing describes the invention including preferred forms thereof. Alterations and modifications as will be obvious to those skilled in the art are intended to be incorporated within the scope of the appended claims.

The invention claimed is:

1. An inductive power transfer system for supplying power to an electrical load located in it living body, the system including:
   a primary power supply located externally of the living body having a primary resonant circuit and being capable of providing an electromagnetic field;
   an inductive power pick-up implanted within the living body having a pick-up resonant circuit and being capable of receiving power from the electromagnetic field provided by the primary power supply to supply power to the electrical load;
   a plurality of reactive components, the reactive components being electrically connected to one or both of the primary resonant circuit and the pick-up resonant circuit;
   a processor unit to increase or decrease the power available to the load by switching one or more of the reactive components into or out of connection with the primary resonant circuit or the pick-up resonant circuit to thereby vary the resonant frequency of the primary resonant circuit or the pick-up resonant circuit, the processor unit being a microprocessor, analogue circuit, programmable logic device or combination of any of the foregoing; and
   wherein at least one of the reactive components is switched into or out of connection with the resonant circuit with which it is connected at a first rate and another reactive component is switched into or out of connection with the resonant circuit with which it is connected at a second rate that is slower than the first rate.

2. An inductive power transfer system as claimed in claim 1 wherein the reactive components are electrically connected to the pick-up resonant circuit.

3. An inductive power transfer system as claimed in claim 1 wherein the reactive components are electrically connected to the primary resonant circuit.

4. An inductive power transfer system as claimed in claim 1 wherein at least one of the reactive components is electrically connected to the pick-up resonant circuit and at least one of the reactive components is electrically connected to the primary resonant circuit.

5. An inductive power transfer system as claimed in claim 4 wherein the resonant frequency for operation of the system is selectable by control of the reactive components between a first operating frequency providing maximum efficiency at a lower power transfer level and a second frequency providing maximum power transfer at a lower efficiency.

6. An inductive power transfer system as claimed in claim 4 wherein the processor unit is able to switch the reactive components to provide a first power transfer level, and to control the reactive components to provide a second power transfer level.

7. An inductive power transfer system as claimed in claim 1 wherein at least one of the reactive includes conducting sections of a coil electrically connected to the primary resonant circuit which may be switched in or out, altering the inductance of the coil and/or to alter the direction of the magnetic field produced by the coil.

8. An inductive power transfer system as claimed in claim 1 wherein the first rate of switching and the second rate of the switching is controlled by the processor unit.

9. An inductive power transfer system as claimed in claim 1 wherein the processor unit is configured to use a combination of a first reactive component and a second reactive component to operate at a lower or higher frequency limit compared to the operating frequency range obtained by using a single reactive component.

10. An inductive power transfer system as claimed in claim 9 wherein the first reactive component is configured to provides a fine tuning of the frequency and the second reactive component is configured to provides discrete changes in frequency hands such that the combined effect is a continuous range of frequency adjustment.

11. An inductive power transfer system as claimed in claim 1 wherein the system includes:
a sensor to provide an indication of temperature in the vicinity of the pick-up, and the processor unit controls switching of the reactive, components in response to the temperature indication provided by the sensor.

12. An inductive power transfer system as claimed in claim 1 wherein the reactive components include a plurality of capacitors of substantially the same value in electrical connection with the pick-up resonant circuit and the processor unit includes a switching means able to connect or disconnect one or more of the capacitors to or from the resonant circuit independently from the state of other capacitors, and whereby the processor unit determines the state of the switching means and compensate for a failure in any capacitor.

13. An inductive power transfer system as claimed in claim 1 wherein the pick-up includes:
a first pick-up coil;
a second pick-up coil;
a resonant capacitor;
a switching matrix able to switch the coils and capacitor to be selectively electrically connected in a plurality of different configurations;
and wherein the processor unit is controllable to provide signals to the switching matrix to provide a required circuit configuration.

14. A method of inductive power transfer for supplying power to an electrical load located in a living body, the method including the steps of:
controlling the power available to the load by controlling a plurality of reactive components electromagnetically coupled with resonant circuits of one or both of a primary resonant circuit located externally of the living body and a pick-up resonant circuit implanted within the living body to vary the resonant frequency of the primary resonant circuit or the pick-up resonant circuit; and
wherein each of the reactive components is associated with a resonant circuit, at least one of the reactive components is switched into or out of connection with the resonant circuit with which it is associated at a first rate and another reactive component is switched into or out of connection with the resonant circuit with which it is associated at a second rate that is slower than the first rate.

15. A method as claimed in 14, wherein the timing of the switching is controlled by the processor unit.

16. A method as claimed in claim 14 including using the reactive component that is switched at the first rate to provide fine tuning and using the reactive component that is switched at the slower rat to provide at discrete jump in one or more frequency bands such that the combined effect is a continuous range of frequency adjustment.

17. A method as claimed in claim 14 where controlling the power includes the steps of selecting a first plurality of reactive components providing maximum efficiency at a lower power transfer level and selecting a second plurality of reactive components providing maximum power transfer at a lower efficiency.

18. A method as claimed in 14 including selectively electrically connecting:
a first pick-up coil;
a second pick-up coil; and
a resonant capacitor;
in a plurality of different configurations to control the power supplied to the load.

19. A method as claimed in claim 18 that includes the step of selecting a configuration that provides power to the load when one of the components fails.

20. A method a claimed in claim 18 that includes the step of selecting a configuration that enables different pick-up coils to be used at different times.

21. A method as claimed in claim 18 that includes the step of selecting a configuration that enables different pick-up coils to be used when supplying different load requirements.

22. The method of claim 18, further comprising the step of selecting a circuit configuration that provides power when one of the coils or capacitors fails.

23. The method of claim 18, further comprising, the step of providing a signal to select circuit configurations that enable different pick-up coils to be used at different times.

24. The method of claim 18, further comprising the step of providing a signal to select circuit configurations that enable different pickup coils to be used when supplying different load requirements.

25. A method of inductive power transfer for supplying power to an electric load located in a living body, the method including the steps of:
providing a primary power supply having a primary resonant circuit and being capable of providing an electromagnetic field;
providing an inductive power pick-up having a pick-up resonant circuit and being capable of receiving power from the electromagnetic field provided by the primary power supply to supply power to an electric load;
using a processor unit to increase or decrease the power available to the load by controlling a first and a second reactive component in electrical connection with the primary resonant circuit or the pick-up coil resonant circuit to thereby vary the resonant frequency of the primary resonant circuit or the pick-up resonant circuit, the processor unit being a microprocessor, analogue circuit, programmable logic device or combination of any of the foregoing;
controlling the first reactive component to vary the resonant frequency of the respective resonant circuit over a plurality of current or voltage cycles; and
controlling the second reactive component to vary the resonant frequency of the respective resonant circuit in each current or voltage cycle; and
wherein at least one of the reactive components is switched into or out of connection with the resonant circuit with which it is connected at a first rate and another reactive component is switched into or out of connection with the resonant circuit with which it is connected at a second rate that is slower than the first rate.

* * * * *